(12) United States Patent
Russell et al.

(10) Patent No.: US 7,094,799 B2
(45) Date of Patent: Aug. 22, 2006

(54) POLYMORPHS OF BICIFADINE HYDROCHLORIDE

(75) Inventors: Brenton William Russell, West Lafayette, IN (US); Rex Alwyn Shipplett, Wolcott, IN (US); Kevin John Halloran, Somerset, NJ (US)

(73) Assignee: DOV Pharmaceutical, Inc., Hackensack, NJ (US)

( * ) Notice: Subject to any disclaimer, the term of this patent is extended or adjusted under 35 U.S.C. 154(b) by 219 days.

(21) Appl. No.: 10/702,397

(22) Filed: Nov. 5, 2003

(65) Prior Publication Data

US 2004/0102638 A1 May 27, 2004

Related U.S. Application Data

(60) Provisional application No. 60/424,982, filed on Nov. 8, 2002.

(51) Int. Cl.
*A61K 31/40* (2006.01)
*C07D 209/52* (2006.01)

(52) U.S. Cl. ...................................... 514/412; 548/452
(58) Field of Classification Search ................ 548/452; 514/412

See application file for complete search history.

(56) References Cited

U.S. PATENT DOCUMENTS

| 4,196,120 A | 4/1980 | Fanshawe et al. |
| 4,231,935 A | 11/1980 | Fanshawe et al. |
| 4,435,419 A | 3/1984 | Epstein et al. |
| 4,504,657 A | 3/1985 | Bouzard et al. |
| 4,521,431 A | 6/1985 | Crookes |
| 6,204,284 B1 | 3/2001 | Beer et al. |

OTHER PUBLICATIONS

Nicholas D. Cheronis, 1958, "Semicro Experimental Organic Chemistry", Chapter 5.*
Brittain, H. G., polymorphism in Pharmaceutical Solids, Drugs and the Pharmaceutical Science; 1999, V. 95, pp. 348-361.*

* cited by examiner

*Primary Examiner*—Kamal A. Saeed
*Assistant Examiner*—Robert Shiao
(74) *Attorney, Agent, or Firm*—Jeffrey J. King; Black Lowe & Graham, PLLC

(57) ABSTRACT

A new polymorphic crystalline form of bicifadine hydrochloride, designated form B, which is more thermodynamically stable than the previously known polymorphic form of bicifadine hydrochloride, designated as form A, methods for preparing said crystalline form B and pharmaceutical compositions containing said crystalline form B.

5 Claims, 1 Drawing Sheet

Infrared Spectrum of Form B Bicifadine Hydrochloride (4000 – 400 cm$^{-1}$)

POLYMORPHS OF BICIFADINE HYDROCHLORIDE

RELATED APPLICATIONS

This application is based upon and claims the benefits of U.S. Provisional Patent Application 60/424,982, filed on Nov. 8, 2002 entitled "Polymorphs of Bicifadine Hydrochloride".

BACKGROUND OF INVENTION

Bicifadine hydrochloride, which is the hydrochloric acid addition salt of

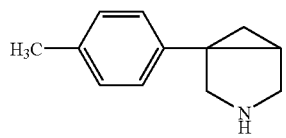

is a non-narcotic analgesic (that is, not morphine-like in action). See U.S. Pat. No. 4,231,935 and U.S. Pat. No. 4,196,120.

Bicifadine hydrochloride, whose chemical name is (±)-1-(4-methylphenyl)-3-azabicyclo[3.1.0]-hexane hydrochloride and whose synonym is racemic 1-(p-tolyl)-3-azabicyclo[3.1.0]-hexane hydrochloride, has been produced as described in Example 36 of U.S. Pat. No. 4,231,935 as pale tan plates shaped crystals. This product has been produced from 1-(p-tolyl)-1,2-cyclopropanedicarboximde. The 1-(p-tolyl)-1,2-cyclopropanedicarboximde was dissolved in an organic solvent, reduced to an amine and converted to the hydrochloride salt to yield a precipitate of crude bicifadine hydrochloride. The crude bicifadine hydrochloride was recovered from the reaction medium by filtration. The crude bicifadine hydrochloride was then recrystallized from an acetonitrile/methanol mixture to give to crystals in the shape of tan plates.

The crystalline form of bicifadine hydrochloride is of particular importance since it is formulated in various oral unit dosage forms as for example as tablets or capsules for the treatment of pain in patients. Variations in crystal structure of a pharmaceutical drug substance may affect the dissolution, manufacturability and stability of a pharmaceutical drug product, specifically in a solid oral dosage form formulation. Therefore it is important to produce bicifadine hydrochloride in a pure form consisting of a single, thermodynamically stable crystal structure. It has been determined that the bicifadine hydrochloride crystal structure produced in accordance with the above procedure, as pale tan plates, is not the most thermodynamically stable polymorphic form. Furthermore, it has been demonstrated that bicifadine hydrochloride of this polymorphic form (hereafter referred to as form A) undergoes conversion to a different polymorphic form when subjected to conventional manufacturing processes, such as grinding and milling. Since form A is not the most thermodynamically stable form of bicifadine hydrochloride, form A could also undergo polymorph conversion over time. Therefore, form A has not been the optimal crystalline form of bicifadine hydrochloride for formulation into pharmaceutical drug products.

SUMMARY

In accordance with this invention, we have discovered that crystalline bicifadine hydrochloride exists in two polymorphic forms, and that the crystalline form produced in U.S. Pat. No. 4,231,935, as pale tan plates, is one of the two polymorphic forms of bicifadine hydrochloride. This polymorphic form is designated as the polymorph form A. Further in accordance with this invention, we have discovered that another new crystalline polymorphic structure of bicifadine hydrochloride exists, wherein the crystals are more thermodynamically stable and do not undergo polymorph conversion when subjected to conventional pharmaceutical manufacturing operations, such as grinding and milling. This new polymorphic form is designated as polymorph form B.

DETAILED DESCRIPTION

Figure 1:
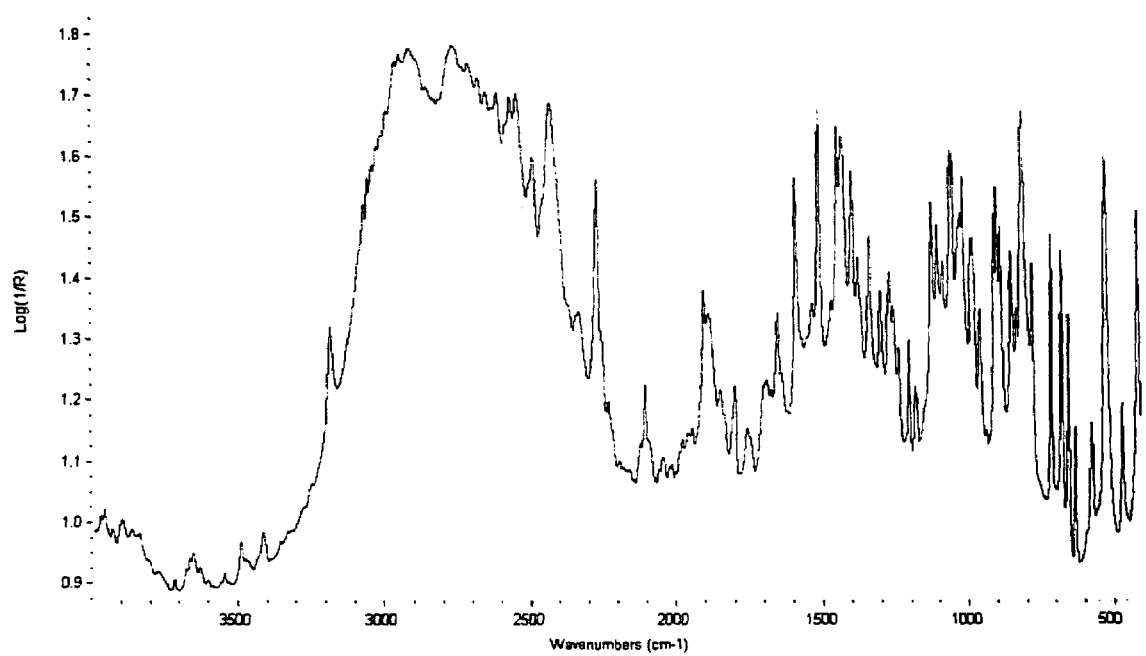
FIG. 1 is the infrared spectrum of the polymorph form B racemic bicifadine hydrochloride as prepared in Example 9.

In accordance with this invention, we have discovered a new polymorphic crystalline form of bicifadine hydrochloride, designated form B, which is more thermodynamically stable than the previously known polymorphic form of bicifadine hydrochloride, designated as form A. Unlike the crystals of polymorph form A, which are in the form of pale tan plates, the crystals of polymorph form B of bicifadine hydrochloride are in the form of blades which range in color from white to off white.

The polymorphs of bicifadine hydrochloride may be characterized by their infrared spectra and/or their x-ray powder diffraction pattern. The relative intensities of the x-ray powder diffraction peaks of a given polymorph may vary depending upon the particle size used to determine the pattern. This is a phenomenon of preferred orientation of the crystals in the sample holder. However with the given polymorph form B of bicifadine hydrochloride of this invention there are certain peaks in this pattern which are typically present no matter the particle size. On the other hand the infrared spectra of a given polymorph, such as the polymorph form B of bicifadine hydrochloride of this invention, will remain relatively constant irrespective of the particle size.

The X-ray powder diffraction (XRPD) analyses of polymorphic forms A and B of racemic bicifadine hydrochloride were performed with a Shimadzu XRD-6000 X-ray powder diffractometer using Cu Kα radiation. The bicifadine was loaded onto the machine as a crystalline powder. The instrument was equipped with a fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A theta-two theta continuous scan at 3°/min (0.4 sec/0.02° step) from 2.5 to 40°2θ was used. A silicon standard was analyzed to check the instrument alignment. Data were collected and analyzed using XRD-6000 v. 4.1.

The X-ray powder diffraction pattern of polymorph form B of racemic bicifadine hydrochloride is given in terms of "d" spacings and relative intensities (I) is as follows (s=strong, m=medium, w=weak, v=very, d=diffuse) and these terms are set forth in Table 1 below:

TABLE 1

Peak Positions, d-Spacings, and Intensities for Form B Bicifadine Hydrochloride

| 2θ (deg) | d (Å) | I[a] |
|---|---|---|
| 5.08 | 17.39 | vs |
| 10.07 | 8.77 | s |
| 15.19 | 5.83 | s |
| 16.83 | 5.27 | s |
| 18.64 | 4.76 | md |
| 18.76 | 4.73 | md |
| 19.64 | 4.52 | w |
| 20.16 | 4.40 | m |
| 21.96 | 4.05 | m |
| 22.37 | 3.97 | s |
| 23.16 | 3.84 | w |
| 24.00 | 3.70 | w |
| 25.27 | 3.52 | d |
| 27.33 | 3.26 | md |
| 27.74 | 3.21 | m |
| 29.00 | 3.08 | m |
| 30.43 | 2.93 | md |
| 31.84 | 2.80 | wd |
| 32.29 | 2.77 | w |
| 35.27 | 2.54 | wd |
| 35.64 | 2.52 | w |

[a]s = strong, m = medium, w = weak, v = very, d = diffuse

The X-ray powder diffraction pattern of form A of bicifadine hydrochloride is set forth in Table 2 in the same terms as in Table 1 as follows:

TABLE 2

XRPD Peak Positions, d-Spacings, and Intensities for Form A Bicifadine Hydrochloride

| 2θ (deg) | d (Å) | I[a] |
|---|---|---|
| 5.35 | 16.50 | vs |
| 10.61 | 8.33 | vs |
| 11.45 | 7.72 | w |
| 15.22 | 5.82 | w |
| 15.93 | 5.56 | w |
| 16.97 | 5.22 | w |
| 18.37 | 4.83 | w |
| 20.04 | 4.43 | md |
| 20.26 | 4.38 | md |
| 21.22 | 4.18 | m |
| 21.89 | 4.06 | s |
| 23.12 | 3.84 | md |
| 23.54 | 3.78 | wd |
| 26.63 | 3.34 | m |
| 27.83 | 3.20 | wd |
| 28.32 | 3.15 | wd |
| 30.67 | 2.91 | wd |
| 32.03 | 2.79 | s |
| 37.57 | 2.39 | w |
| 38.20 | 2.35 | w |

[a]s = strong, m = medium, w = weak, v = very, d = diffuse

Table 1 and Table 2 represent the XRPD pattern of the peak positions of bicifadine hydrochloride form B and form A respectively having reduced particle size. The results in these tables demonstrate the difference between the XRPD pattern of form A and form B at a reduced particle size. However, there are key major peaks at given angles in this pattern which are unique to the given polymorph form B of bicifadine hydrochloride and are typically present in XRPD pattern of polymorph form B irrespective of its particle size. These angles, expressed as 2θ(deg), locating these major peaks which characterize the polymorph form B, using Cu Kα radiation, are:

5.08;
10.07;
20.16;
25.17; and
30.43

The infrared spectra was obtained for each of the samples using a Magna-IR 860® Fourier transform infrared (FT-IR) spectrophotometer (Thomas Nicolet) equipped with an Ever-Glo mid/far IR source, an extended range potassium bromide (KBr) beamsplitter, and a deuterated triglycine sulfate (DTGS) detector. The spectrophotometer measured the intensity of infrared light bands of each of the samples at given wavelengths. A diffuse reflectance accessory (the Collector™, Thermo Spectra-Tech) was used for sampling. Each spectrum represents 256 co-added scans collected from 400–4000 cm-1 at a spectral resolution of 4 cm-1. Sample preparation consisted of placing the sample of powder containing crystals in either polymorph form A or form B into a 13-mm diameter cup and leveling the material with a frosted glass slide. A background data set was acquired with an alignment mirror in place. The reflectance R is the ratio, at a given wavenumber, of the light intensity of the sample/light intensity of the background set. FIG. 1 sets forth the infrared spectrum of polymorph B in which the abscissa is wavenumbers $cm^{-1}$ and the ordinate is Log(1/R). A Log 1/R(R=reflectance) spectrum acquired by taking a ratio of these two data sets(the sample and the background light intensities) against each other. The infrared spectrum of polymorph B or racemic bicifadine hydrochloride as a dry crystalline powder, as given in Table 3, showed the following peaks which characterized this polymorph.

TABLE 3

Infrared Peak Positions for Form B Bicifadine Hydrochloride. All values in wavenumbers ($cm^{-1}$)

| | |
|---|---|
| 3185 | 1111 |
| 2769 | 1022 |
| 2437 | 963 |
| 2276 | 904 |
| 2108 | 891 |
| 1908 | 856 |
| 1804 | 818 |
| 1658 | 783 |
| 1596 | 719 |
| 1518 | 684 |
| 1453 | 660 |
| 1403 | 637 |
| 1343 | 580 |
| 1305 | 532 |
| 1274 | 475 |
| 1209 | 422 |
| 1131 | |

The infrared spectrum polymorph A of racemic bicifadine hydrochloride in dry crystalline powder showed the following main peaks which characterize this polymorph.

TABLE 4

Infrared Peak Positions For Form A Bicifadine Hydrochloride. All values in wavenumbers ($cm^{-1}$)

| | |
|---|---|
| 3949 | 1088 |
| 2923 | 1068 |
| 2431 | 1050 |
| 2280 | 900 |
| 2091 | 825 |
| 1895 | 781 |
| 1790 | 714 |
| 1595 | 689 |

TABLE 4-continued

Infrared Peak Positions For Form A Bicifadine Hydrochloride.
All values in wavenumbers (cm$^{-1}$)

| | |
|---|---|
| 1522 | 652 |
| 1430 | 574 |
| 1376 | 533 |
| 1233 | 437 |
| 1130 | |

Table 3 and Table 4 provide the complete patterns of the infrared peak positions with respect to polymorph form B and polymorph form A of bicifadine hydrochloride respectively. However, there are certain key peaks, within this pattern, which are unique to the polymorph form B of bicifadine hydrochloride and are sufficient to characterize this polymorph. These peaks, expressed in wavenumbers (cm$^{-1}$), are:

2108;
891;
856;
719; and
660.

In accordance with this invention, we have found means for forming bicifadine hydrochloride having the polymorph B crystal structure. The known methods for preparing racemic bicifadine hydrochloride produce polymorph form A since that is the polymorph crystal structure first produced. One means for forming polymorph form B from polymorph form A is to provide kinetic energy to polymorph form A which is produced normally. This kinetic energy can be applied to polymorph form A especially at low temperatures, generally from about −200° C. to about 50° C., preferably from about −200° C. to about 35° C., most preferably from about −200° C. to about 0° C. In carrying out this conversion, any method of applying kinetic energy, such as by means of stirring, grinding or milling, to the normal crystalline polymorph form A of bicifadine hydrochloride can be utilized. The grinding or milling can be applied at room temperature. However, this conversion, using kinetic energy, is more efficiently carried out at lower temperatures. For example a kinetic energy method for conversion of polymorph form A into polymorph form B is to utilize solid crystals of polymorph A and apply stirring or grinding to these crystals while maintaining the temperature at no greater than about 35° C., generally from about −200° C. to 0° C. Low temperatures can be utilized while supplying kinetic energy such as by grinding under a liquid nitrogen atmosphere.

Another method of converting polymorph form A into polymorph form B is by crystallization of polymorph form B from a heated solution and allowing said solution to cool for sufficient amount of time to form said polymorph B. Polymorph form A crystals are generally poorly soluble in organic solvents at room temperature. However, they become soluble when heated. In accordance with this conversion, the polymorph form A crystals of bicifadine hydrochloride are mixed with an organic solvent, having a boiling point of at least 50° C. to form a slurry. In carrying out this conversion any conventional organic solvent having a boiling point of at least 50° C. can be utilized. The slurry is then heated to a temperature at which said slurry is a clear solution, and this solution is cooled to a temperature of at most about 35° C., preferably between about 0° C. to about 20° C. The cooled solution is maintained at a temperature of at most about 35° C. for a period of time sufficient to allow said polymorph B to form as a pure crystalline form free from the presence of the polymorph form A. If desired, cooling can be carried out with stirring. During cooling the mixture should be monitored to allow sufficient time for crystalline polymorph B to form from the mixture. In this procedure the time of conversion is also enhanced by adding "seed crystals" of form B to the mixture as it cools.

In addition polymorph form B can be produced from bicifadine hydrochloride form A or from a mixture of form A and B of bicifadine hydrochloride by forming a slurry of bicifadine hydrochloride either as form A or a mixture of form A and B in an inert organic solvent and agitating the slurry at a temperature of at most about 35° C. Any conventional inert organic solvent can be used in forming this slurry. The agitation is carried out for a period of time sufficient to convert the bicifadine hydrochloride to polymorph form B. This period could be as long as 24 hours. This time period could be shortened by using "seed" crystals of polymorph form B and/or using temperatures lower than 35° C.

The form B polymorph produced by any of the above methods can be in pure form without the presence of any other polymorphic forms of bicifadine hydrochloride as determined by XRPD or Infra-Red. In this manner the pure racemate of the polymorph B of bicifadine hydrochloride is produced without the presence of the other polymorphic forms of racemic bicifadine hydrochloride.

The polymorph form B of bicifadine hydrochloride can be administered to human patients for reducing pain. This is accomplished by treating the patient in need of the treatment who is suffering from said pain with a composition containing bicifadine hydrochloride having the crystalline structure of polymorph B and an inert carrier or diluent, said composition being administered in an effective amount to alleviate said pain. In accordance with this invention, racemic bicifadine hydrochloride in its crystalline polymorph form B is administered in an effective amount to alleviate pain. Any effective amount of bicifadine hydrochloride needed to alleviate pain can be utilized in this composition. In general oral dosages of from about 0.5 mg/kg to about 20 mg/kg per day are used. However the amount of racemic bicifadine hydrochloride in its crystalline polymorph form B in the oral unit dose to be administered will depend to a large extent on the amount of pain and the weight of the patient and of course be subject to the physician's judgment. In accordance with this invention, the oral unit dosage form containing racemic bicifadine hydrochloride in its crystalline polymorph form B can be administered at a dosage of from 25 to 600 mg either once or twice a day or as needed. For patients of from about 60 kg to about 80 kg, unit oral dosage forms containing from about 100 mg to about 600 mg can be utilized, with dosages of about 200 to 400 mg being generally preferred. This oral unit dosage form can be administered once or twice a day or as needed. For less pain and for patients whose weight is below 60 kg an oral unit dosage form containing from about 25 mg to about 200 mg can be utilized either once or twice a day or more depending on the patients needs In the compositions of this invention, any conventional pharmaceutically acceptable carriers or diluents can be utilized. For oral administration, the pharmaceutical composition may be any of the conventional oral unit dosage forms, for example tablets, capsules, powders, solutions, syrups or suspensions prepared by conventional excipients. Therefore, oral administration of the compositions may take the form of tablets or capsules, lozenges, etc. formulated in the conventional manner. Each of these formulations contain the racemic bicifadine hydrochloride in the form of its crystalline polymorph B. Generally, it is preferred to use polymorph form B bicifadine hydrochloride without the presence of any bicifadine hydrochloride in its crystalline polymorph A state in these formulations. Polymorph form B is the thermodynamically stable polymorph of bicifadine hydrochloride and does not undergo crystal interconversion during manufacturing and over the anticipated commercial shelf-life of the drug product formulations If desired, the racemic bicifadine hydrochloric in its crystalline polymorph form B can be administered in a controlled release form by use of the hydrophilic slow release polymer, hydroxypropyl methyl cellulose, in the oral unit dosage form. Any hydrophilic slow release polymer can be utilized, such as hydroxypropyl methyl cellulose polymer having a viscosity in the range of about 100 cps to about 100,000 cps.

In accordance with this invention, the composition in the oral unit dosage form may contain a carrier. Suitable carriers common to pharmaceutical formulation technology include, but are not limited to microcrystalline cellulose, lactose, sucrose, fructose, glucose dextrose, or other sugars, di basic calcium phosphate, calcium sulfate, cellulose, methylcellulose, cellulose derivatives, kaolin, mannitol, lactitol, maltitol, xylitol, sorbitol, or other sugar alcohols, dry starch, dextrin, maltodextrin or other polysaccharides, inositol, or mixtures thereof.

The preferred unit oral dosage form for use in this invention is a tablet. Any conventional method of preparing pharmaceutical oral unit dosage forms can be utilized in preparing the unit dosage forms of this invention. The pharmaceutical oral unit dosage forms, such as the tablets, contain one or more of the conventional additional formulation ingredients. These ingredients are selected from a wide variety of excipients known in the pharmaceutical formulation art. According to the desired properties of the oral dosage form, any number of ingredients may be selected alone or in combination for their known use in preparing such dosage forms as tablets. Such ingredients include, but are not limited to release modifying agents, glidants, compression aides, disintegrants, lubricants, binders, flavors, flavor enhancers, sweeteners and preservatives.

Suitable lubricants include stearic acid, magnesium stearate, talc, calcium stearate, hydrogenated vegetable oils, sodium benzoate, leucine carbowax, magnesium lauryl sulfate, colloidal silicon dioxide and glyceryl monostearate. Suitable glidants include colloidal silica, fumed silicon dioxide, silica, talc, fumed silica, gypsum and glyceryl monostearate.

In accordance with this invention, any conventional means for preparing standard oral unit dosage forms can be utilized. In forming tablets, the blend can be compressed by conventional means to produce tablets formed from bicifadine hydrochloride in its crystalline polymorph form B. The term "tablet" as used herein is intended to encompass compressed pharmaceutical dosages formulations of all sizes and shapes whether coated or uncoated. Substances which may be used for coating include hydroxypropyl cellulose, titanium oxide, talc, sweeteners and colorants.

EXAMPLES

Example 1

Preparation of Racemic Bicifadine Hydrochloride

A 300 gal reactor was charged with water (150 L) and sodium hydroxide (100 kg) and the solution was cooled to 10±5° C. A second 300 gal reactor was charged with chloroform (203 kg), benzyltriethylammonium chloride (8.2 kg) and 4-tolualdehyde (99 kg). The reaction mixture was heated to gentle reflux and the sodium hydroxide solution was added at a rate to maintain reflux. After the addition, which took approximately 6 hours, reflux was continued for at least another 3 hours. The hot reaction solution was added to 500 L of cold water (5° C.) and the mixture was stirred for approximately 15 minutes. The phases were allowed to separate. The lower organic layer was transferred to a holding tank. The aqueous layer was washed with chloroform (1×72 kg then 4×20 kg) to remove any unreacted 4-tolualdehyde. The combined organic phases were saved for later reprocessing. The aqueous layer was acidified to pH 1 with concentrated HCl (48 kg) to precipitate 4-methylmandelic acid as a yellow granular solid. After stirring the slurry overnight the product was isolated by filtration, washed with water (150 L), and dried in vacuo at 60° C. for at least 24 hours. The process gives approximately 80 kg of 4-methylmandelic acid. To the chloroform extracts from above was added benzyltriethylammonium chloride (approximately 4.5 kg) and the mixture is heated at reflux. To the reaction mixture was added a solution of sodium hydroxide (50 kg) in water (75 L). After the addition was complete (at least 1.5 hrs) the reaction mixture was heated at reflux overnight. The hot reaction mixture was added to a reactor containing 250 kg of water at 5±5° C. The layers were allowed to separate and the lower organic layer was discarded. The aqueous layer was washed with chloroform (1×36 kg then 4×10 kg). The pH of the aqueous layer was adjusted to 0.5 to 1.5 with concentrated hydrochloric acid. The slurry was stirred overnight at 25±5° C. The product was isolated by filtration, washed with water (50 L) and dried in vacuo for at least 24 hours. This produced an additional 34 kg of 4-methylmandelic acid.

Thionyl chloride (179 kg) was added over a two hour period to a mixture of 4-methylmandelic acid (110 kg) in toluene (102 kg) containing dimethylformamide (730 ml). On completion of the feed, the mixture was stirred at ambient temperature for a further 3 hours. Methanol (362 kg) was added over 2 hours at such a rate as to control gas evolution. The excess methanol was removed by distillation at atmospheric pressure. The distillation was continued until the internal pot temperature reached at least 85° C. Toluene (577 kg) was charged to the residue and the temperature was adjusted to 50±5° C. Water (152 L) was added, the mixture was stirred for 15 minutes then allowed to settle for a further 30 minutes. The aqueous layer was discarded and the toluene layer was successively washed with 10% aqueous sodium bicarbonate (186 kg) and water (169 kg). The toluene solution was dried by azeotropic distillation until the water content was <0.1%. Methyl acrylate (55 kg) was added at 45±5° C. to the anhydrous toluene solution of racemic methyl 2-chloro-2-(p-tolyl) acetate. Sodium methoxide (32.1 kg) was added in approximately 16 equal portions over a 3 hour period. On completion of the addition, the reaction mixture was held at 45±5° C. for a further 3 hours. The reaction mixture was washed successively with 5% HCl (215 L) and water (169 L). The toluene was removed by distillation under reduced pressure up to a pot temperature greater than 95° C. The residue was cooled to 50±5° C. and treated with methanol (137 kg) and water (450 L). Potassium hydroxide (approximately 39 kg) was added and the mixture was heated to reflux for about 6 hours. The alcohol was removed by distillation up to a maximum pot temperature of 98–100° C. The resulting solution was cooled to less than 25° C. and acidified to pH 1 with a mixture of concentrated HCl (86 kg) and water (150 L). The mixture was stirred. The precipitate was collected by filtration, washed well with water (36 L) and air dried to give crude 1-(4-methylphenyl)-1,2-cyclopropranedicarboxylic acid.

Crude 1-(4-methylphenyl)-1,2-cyclopropanedicarboxylic acid (approximately 184 kg)) was slurried in water (900 L) at ambient temperature in a 300 gal reactor. Sodium hydroxide was added in portions until pH of at least 10 was obtained. After a solution has been obtained, the pH was adjusted to approximately 5.5 by the cautious addition of concentrated hydrochloric acid (19.8 kg). After cooling to 25° C., methylene chloride was added (100 kg), the mixture was stirred for 30 minutes, and then the lower layers discarded. This washing procedure was repeated with a further quantity of methylene chloride (100 kg). The aqueous solution was then acidified to pH 1 with concentrated hydrochloric acid (70 kg). After stirring for approximately 3 hours at 20–25° C., the pale yellow solid was filtered. The cake was washed with water (2×100 L) and dried in vacuo at 60° C. for at least 24 hours to give approximately 74 kg of 1-(4-methylphenyl)-1,2-cyclopropanedicarboxylic acid.

A mixture of purified 1-(4-methylphenyl)-1,2-cyclopropanedicarboxylic acid (58 kg), toluene (465 kg) and urea (23.8 kg) was heated to reflux and the mixture held at reflux until the reaction was complete. On completion of the reaction period, the solution was cooled to 80–90° C. and washed with water (69 L). The lower aqueous layer was discarded. In this way (±)-1-(4-methylphenyl)-3-azabicyclo[3.1.0]hexan-2,4-dione was obtained as a solution in toluene.

The toluene solution was heated at reflux to azeotropically remove water until a moisture content of <0.1% was obtained. The solution was cooled to 50±5° C. and Vitride T (186.6 kg) was added slowly to control foaming (the reaction exotherms to approximately 60° C.). On completion of the addition, the contents of the reactor were heated to 95±5° C. and maintained at that temperature until the reaction was complete. After cooling to 20±10° C., the batch was added slowly to a solution of sodium hydroxide (108 kg) in water (418 L). After a short period of agitation at 40±10° C., the layers were separated and the lower aqueous layer was discarded. The organic phase was washed with water (2×836 L). The lower aqueous layers were discarded and the organic layer was dried azeotropically until the moisture content was <0.1%. After cooling to <20° C. the dry toluene solution was treated with anhydrous hydrogen chloride until the pH of an aqueous extract was ≦6.5. The excess HCl was removed by sparging with nitrogen and the slurry was stirred for at least 1 hour at about 10° C. prior to isolation by filtration. The slurry was filtered. The cake was washed with acetone (2×25 L) and dried in vacuo until the moisture content was <3%. The yield was 31.8 kg of crude bicifadine hydrochloride as an off-white crystalline solid.

The crude bicifadine HCl was added to isopropyl alcohol (490 kg). The reaction mixture was heated to a gentle reflux. The solution was treated with activated carbon (2.4 kg) and Celite (3.4 kg). The solution was refluxed for 1 to 2 hours, filtered to remove Celite and carbon, and then passed through a 0.2µ filter. The solution was cooled to ≦20° C. and held at that temperature overnight. The product was isolated by filtration, washed with cold isopropyl alcohol (2×23 L) and finally acetone (2×23 L). The product was dried in vacuo at 50° C. to a moisture content of <0.1% to give approximately 24 kg of bicifadine hydrochloride as a white to off-white crystalline solid. This solid was used in Examples 7 through 9 hereinafter.

Example 2

Preparation of Racemic Bicifadine Hydrochloride

Each of two 50 L flasks was charged with 12 L of toluene, 3000 g of methyl-α-chloro-p-tolylacetate and 1300 g of methyl acrylate. Sodium hydride, 60% in mineral oil, (725 g) was added to each flask and the resulting slurries were stirred at room temperature for approximately 30 minutes. The reaction mixtures were cooled to −10° C. While maintaining a temperature of approximately −10° C., 636 mL of methanol was added to each flask along with 1.2 L of methyl tert-butyl ether. The reaction mixtures were stirred at room temperature for a minimum of 12 hours. After observing that the reaction mixtures change from a gray slurry to a clear orange solution and confirming that the starting material was ≦5%, 1.6 L of water was added to each flask. The mixtures were stirred for an additional 10 minutes. Both reaction mixtures were combined into a single 40 L separatory funnel and the aqueous and organic layers were allowed to separate. Each layer was drained into one of two s-gallon pails. The aqueous layer was poured back into the separatory funnel and extracted with ethyl acetate (2×2 L & 1×1 L). The aqueous layer was discarded. The organic layers were combined, returned to the separatory funnel and washed with 1 L of water. The organic layer was drained in equal amounts into the two 5-gallon pails. To each pail, 250 g of charcoal and 250 g of magnesium sulfate were added and the mixture was stirred until well mixed. The material was filtered and washed with ethyl acetate (2×500 mL). The reaction mixture was concentrated on a Buchi Rotavapor to a light yellow oil at 60° C. The oily solution was transferred to a 22 L flask and placed in a cooling bath. While stirring, 10 L of ether was added and the solution was cooled to 0° C. until solids began to precipitate. The solution was then cooled to <−20° C. and stirred for approximately 1.5 hours. The solids were filtered onto an 18" crock filter using a polypropylene filter pad, washed with ethyl ether (3×2 L) and transferred to Pyrex drying trays. The dimethyl-1-(4-methylphenyl)-1,2-cyclopropanedicarboxylate was dried at 25° C. in vacuo.

Each of two 22 L flasks were charged with 9 L of water, 2250 g of dimethyl-1-(4-methylphenyl)-1,2-cyclopropanedicarboxylate and 2.25 L of ethyl alcohol. A 50% sodium hydroxide solution (1.2 L) was added to each flask and the reaction mixtures heated to and held at reflux for approximately 1 hour and 15 minutes. After confirming that the dimethyl-1-(4-methylphenyl)-1,2-cyclopropanedicarboxylate was ≦5%, the reaction mixtures were stirred at approximately 75° C. Both reaction mixtures were transferred into a single 30-gallon crock. Ice was added and the reaction mixture cooled to ≦10° C. The mixture was acidified to pH 1 using 4 L of concentrated hydrochloric acid and the stirred for a minimum of 30 minutes. The solids were filtered onto a crock filter with a filter pad. The filter cake was dissolved in 12 L of ethyl acetate and the layers separated. The organic layer was dried with magnesium sulfate and filtered through a Buchner funnel into a 22 L filter flask. The material was concentrated using a Buchi Rotavapor to a volume of 8 L, diluted with 10 L of hexane and cooled with stirring to 0° C. The solids were filtered and washed with hexane (3×2 L). The 1-(4-methylphenyl)-1,2-cyclopropanedicarboxylic acid was transferred to Pyrex drying trays and dried for a minimum of 12 hours at 35° C. in vacuo.

Each of two 22 L flasks were charged with 14 L of 2-methoxyethyl ether [diglyme], 1750 g of 1-(4-methylphenyl)-1,2-cyclopropanedicarboxylic acid and 716 g of urea. The reaction mixture was heated to approximately 155° C. for at least 12 hours. After confirming that the starting material was ≦5%, both reaction mixtures were transferred to a 55-gallon crock containing approximately 40 Kg of ice and cooled to room temperature. This mixture was diluted with water to a total volume of 100 L and stirred for approximately 4 hours. The mixture was filtered onto a crock filter (18") using a polypropylene filter pad. The solids are washed with water (3×2 L), transferred to a 5-gallon pail and dissolved in 12 L of ethyl acetate. The solution was poured into a 40 L separatory funnel, and the layers were allowed to separate. The aqueous and organic layers were each drained into one of two 5-gallon pails, and the aqueous layer was poured back into the separatory funnel where it was extracted with ethyl acetate (2×1 L). The aqueous layer was discarded and the organic layers combined. Charcoal (500 g) and magnesium sulfate (500 g) were added to the organic layer and the resulting mixture was stirred until well mixed. The solution was filtered through a Buchner funnel (18.5 cm) using a Whatman GF filter pad and the solids were washed with ethyl acetate (2×500 mL). The filtrate was concentrated using a Buchi Rotavapor with a bath temperature of approximately 60° C. until the first crystals were seen or a total volume of 5 L was achieved. The residue from this concentration was transferred to a 5-gallon pail and stirred. The slurry was diluted with 12 L of hexane and stirred at room temperature for 2 hours. The solids were filtered onto a crock filter (18") using a polypropylene filter pad and washed with hexane (3×2 L). The 1-(4-methylphenyl)-3-azabicyclo [3.1.0]hexan-2,4-dione was transferred to Pyrex drying trays and dried at 35° C. in vacuo for a minimum of 12 hours.

Each of two 50 L flasks were charged with 12 L of toluene and 1250 g of 1-(4-methylphenyl)-3-azabicyclo [3.1.0] hexan-2,4-dione. Sodium bis(2-methoxyethoxy) aluminum hydride (5700 mL of 70% Red Al) was added to each flask and the reaction mixtures were heated to reflux for 3 hours. After confirming that the starting material was ≦5%, the reaction mixtures were cooled to <60° C. using an ice/water bath. To a 30-gallon crock, an ice/water mixture (6.4 kg water, 4.4 kg ice) was charged with 2.2 L of sodium hydroxide, 50% solution and the temperature adjusted to approximately 0° C. by adding ice. This mixture was stirred and both reaction mixtures were poured into it. The temperature was lowered to <20° C. by adding ice and the resulting mixture stirred for a minimum of 2 hours. The solution was transferred into a 40 L separatory funnel. The layers were allowed to separate and each layer was drained into one of two 5-gallon pails. The aqueous layer was extracted with ethyl acetate (3×2 L) and discarded, and the organic extracts are combined and washed with water (3×2 L). The aqueous washes were discarded. Into a 2-gallon pail containing 6 L of water, sodium chloride was added until the solution becomes saturated (brine). The organic extracts were washed with brine (3×2 L) and the aqueous washes were discarded. The organic layer was drained in equal amounts into the 5-gallon pails. 250 g of charcoal and 250 g of magnesium sulfate were added to each pail and the resulting mixtures were stirred until well mixed. These solutions were filtered through a Buchner funnel (18.5 cm) using a Whatman GF filter pad. The solids were washed with ethyl acetate (2×500 mL), and the filtrate was concentrated on a Buchi Rotavapor to a total volume of approximately 12 L at a temperature of approximately 60° C. The 20 L Buchi flask was transferred to a cooling tub and stirred rapidly. While maintaining a temperature of <20° C., anhydrous HCl gas was bubbled into the reaction mixture until a pH of 2–3 was reached. The mixture was stirred for an additional 2 hours at <10° C., then placed in a freezer for no less than 12 hours. The solids were filtered onto a crock filter (18") using a polypropylene filter pad and washed first with hexane (3×2 L) and with acetone (3×2 L). The crude bicifadine hydrochloride was transferred to Pyrex drying trays and air dried for a minimum of 2 hours.

Each of four 22 L flasks were charged with approximately 1500 g of crude bicifadine hydrochloride. Isopropyl alcohol (6–10 mL/g) was added and the materials stirred and heated to reflux. Once a clear solution at reflux was achieved, 200 g of charcoal was added to each flask. The solutions were stirred for approximately 10 minutes and filtered through a Buchner funnel (10"), using a polypropylene pad with GF filter on top of it, into a 20 L filter bottle. The resulting filtrates were transferred to a 30-gallon PE crock and stirred at room temperature for a minimum of 3 hours. The crock was placed in a cold room for a minimum of 12 hours. The solids are filtered onto a crock filter (18") using a polypropylene filter pad and washed with acetone (4×2 L). The product of the step, bicifadine hydrochloride, was dried at 50° C. in vacuo until a loss on drying of <1% was achieved. This material was used in Example 6.

Example 3

Conversion to Bicifadine Hydrochloride Form B

Racemic bicifadine hydrochloride as a mixture of polymorphic forms A and B, was added to isopropyl alcohol in a sufficient quantity to form a slurry. The slurry was subjected to agitation, such as mixing, at a temperature less than 30° C. After one day, the product was isolated by filtration and dried at 50° C. in vacuo until loss on drying of <1% was achieved. The material produced was bicifadine hydrochloride polymorphic form B.

Example 4

Conversion to Bicifadine Hydrochloride Form B

Twenty grams of racemic bicifadine hydrochloride as a mixture of polymorphic forms A and B, were added to 60 ml of isopropyl alcohol to slurry. The slurry was stirred for 24 hours at a temperature of about 30° C. The product was isolated by filtration and dried in vacuo. The material produced was bicifadine hyrochloride polymorphic form B, with no detectable presence of polymorphic form A.

Example 5

In Example 5, bicifadine hydrochloride in its polymorphic crystalline form was prepared and crystallized from acetonitrile/methanol as set forth in Example 36 of U.S. Pat. No. 4,231,935. The bicifadine hydrochloride in the samples, i.e., samples 1–5 in Table 5, were recrystallized by evaporation as described below.

Evaporation

The following volume-volume mixtures of acetonitrile-methanol were prepared: 9:1, 2:1, 1:1, 1:2, and 1:9. Weighed amounts of form A bicifadine hydrochloride (approximately go mg) were treated with aliquots of a solvent mixture until a clear solution resulted. Each solution was filtered through a 0.2 micron nylon syringe into a clean vial. The vials were covered with aluminum foil perforated with pinholes and placed under a fume hood to allow evaporation. When the solvent had fully evaporated, the solids were recovered.

The results as to the polymorph obtained are given in Table 5. These results were obtained by using the X-ray powder diffraction technique (XRPD) described above.

TABLE 5

| Sample No. | Solvent Ratio (Acetonitrile:Methanol) | Crystallization Method | XRPD Result |
|---|---|---|---|
| 1 | 9:1 | Evap. | A |
| 2 | 2:1 | Evap. | A |
| 3 | 1:1 | Evap. | A |
| 4 | 1:2 | Evap. | A |
| 5 | 1:9 | Evap. | A |

As in Table 5, simple recrystallization of the product of Example 36 of U.S. Pat. No. 4,231,935 in accordance with the procedure, by evaporation produced bicifadine hydrochloride form A.

Example 6

Preparation of Form A

Bicifadine hydrochloride (20.1 g), as prepared in Example 2, was heated and stirred in isopropyl alcohol (365 mL), resulting in a clear solution at 80° C. The solution was cooled to 55° C., resulting in a slurry. The product was filtered off and dried at ambient temperature to give form A bicifadine hydrochloride.

Example 7

Preparation of Form A

A measured amount of ethanol (1 mL) was saturated with bicifadine hydrochloride (97 mg), produced as a crystalline solid in Example 1, was placed in a vial on a heated stir plate set to 80° C. The solution was filtered directly into a vial containing 1 mL of toluene cooled to −20° C. The mixture was placed in a −20° C. freezer for 15 minutes, resulting in precipitation. The product was filtered off and dried under reduced pressure at ambient temperature to give form A bicifadine hydrochloride.

Example 8

Preparation of Form B

Form A bicifadine hydrochloride (3.99 g), produced as a crystalline solid in Example 1, was heated and stirred in isopropyl alcohol (50 mL), resulting in a clear solution at 82° C. The solution was cooled to ambient temperature, resulting in a thick slurry. The stirring mechanism was shut off, and the mixture sat at ambient temperature for two days. The solids, white to off-white blades, were recovered and air-dried to give form B bicifadine hydrochloride.

Example 9

Preparation of Form B

Form A bicifadine hydrochloride, produced as a crystalline solid in Example 1, (approximately 1 g) was charged to a small stainless steel cylinder. A stainless steel rod was added and the cylinder was capped. The cylinder was installed in a SPEX/Centriprep Model 6750 freezer mill filled with liquid nitrogen. The sample was milled for 2 minutes at a time, with 2-minute intermissions for a grind time of 6 minutes. The tank was refilled with liquid nitrogen, and the cycle was repeated, for a total grind time of 12 minutes. The process resulted in complete conversion to form B bicifadine hydrochloride without the detectable presence of any form A bicifadine hydrochloride

Example 10

The Instability of Form A on Grinding

Form A bicifadine hydrochloride (207 mg) was charged to a small stainless steel cylinder. A stainless steel ball was added, the cylinder capped, and the unit shaken on a Retsch Mixer Mill (Type MM 200) at 5-minute intervals at a frequency of 30/s for a total of 20 minutes. The milled material was then removed and analyzed by XRPD. The process resulted in partial conversion to form B bicifadine hydrochloride.

Example 11

The Stability of Form B on Grinding

Form B bicifadine hydrochloride (111 mg) was charged to a small stainless steel cylinder. A stainless steel ball was added, the cylinder capped, and the unit shaken on a Retsch Mixer Mill (Type MM 200) at 5-minute intervals at a frequency of 30/s for a total of 20 minutes. The milled material was then removed and analyzed by XRPD. The milled solid remained form B.

What is claimed is:

1. A solid composition comprising bicifadine hydrochloride polymorph form B substantially free of bicifadine hydrochloride polymorph form A, said solid composition comprising solid crystals of form B having a distinct infrared profile characterized by one or more of the following infrared spectrum peaks in wavenumbers (cm$^{-1}$):

| | |
|---|---|
| 3185 | 1111 |
| 2769 | 1022 |
| 2437 | 963 |
| 2276 | 904 |
| 2108 | 891 |
| 1908 | 856 |
| 1804 | 818 |
| 1658 | 783 |
| 1596 | 719 |
| 1518 | 684 |
| 1453 | 660 |
| 1403 | 637 |
| 1343 | 580 |
| 1305 | 532 |
| 1274 | 475 |
| 1209 | 422 |
| 1131 | | and a distinct x-ray powder diffraction (XRPD) profile characterized by one or more of the following XRPD peaks expressed in terms of "d" spacings and relative intensities I (s =strong, m=medium, w=weak, v=very, d=diffuse)

| 2θ (deg) | d (Å) | $I^a$ |
|---|---|---|
| 5.08 | 17.39 | Vs |
| 10.07 | 8.77 | S |
| 15.19 | 5.83 | S |
| 16.83 | 5.27 | S |
| 18.64 | 4.76 | Md |
| 18.76 | 4.73 | Md |
| 19.64 | 4.52 | W |
| 20.16 | 4.40 | M |
| 21.96 | 4.05 | M |
| 22.37 | 3.97 | S |
| 23.16 | 3.84 | W |
| 24.00 | 3.70 | W |
| 25.27 | 3.52 | D |
| 27.33 | 3.26 | Md |
| 27.74 | 3.21 | M |
| 29.00 | 3.08 | M |
| 30.43 | 2.93 | Md |

-continued

| 2θ (deg) | d (Å) | $I^a$ |
|---|---|---|
| 31.84 | 2.80 | Wd |
| 32.29 | 2.77 | W |
| 35.27 | 2.54 | Wd |
| 35.64 | 2.52 | W. | s = strong, m = medium, w = weak, v = very, d = diffuse

2. The solid composition of claim 1, which comprises a tablet.

3. The solid composition of claim 1, which comprises a capsule.

4. The solid composition of claim 1, wherein said tablet or capsule comprises said polymorph B crystalline form in a unit dosage amount of between 25 mg to 600 mg.

5. The solid composition of claim 1, wherein said tablet or capsule comprises said polymorph B crystalline form in a unit dosage amount of between 200 mg to 400 mg.

* * * * *